United States Patent [19]

Awazu et al.

[11] Patent Number: 5,207,853
[45] Date of Patent: May 4, 1993

[54] METHOD OF MANUFACTURING INJECTION NEEDLES

[75] Inventors: Fumio Awazu, Otsu; Hideo Kuwabara, Kustasu, both of Japan

[73] Assignee: Nissho Corporation, Osaka, Japan

[21] Appl. No.: 735,972

[22] Filed: Jul. 25, 1991

[30] Foreign Application Priority Data

Jul. 30, 1990 [JP] Japan .................. 2-201757

[51] Int. Cl.⁵ .............................................. A61M 5/32
[52] U.S. Cl. ................................. 156/293; 156/294; 604/263; 206/365
[58] Field of Search ................ 156/293, 294; 604/263, 604/272; 206/365; 29/234, 525, 272

[56] References Cited

U.S. PATENT DOCUMENTS

| | | | |
|---|---|---|---|
| 4,413,992 | 11/1983 | Soika | 604/263 |
| 4,944,397 | 7/1990 | Miller | 604/263 X |
| 4,976,701 | 12/1990 | Ejlersen et al. | 206/365 X |

Primary Examiner—Jeff H. Aftergut
Attorney, Agent, or Firm—Armstrong, Westerman, Hattori, McLeland & Naughton

[57] ABSTRACT

A method of manufacturing an injection needle having a hub and a cannula whose back end terminates within the hub. The method comprises the step of mounting the hub on a first subassembly jig, inserting the cannula into a center hole of the hub, applying an adhesive to a bonding area of the hub and cannula, curing the adhesive, dismounting the hub-cannula assembly from the first subassembly jig, applying silicone-containing-liquid to the back end, mounting the hub-cannula assembly on a second subassembly jig removing excess amount of silicone-containing-liquid within the cannula, covering the front end with a cap, housing the hub-cannula-cap assembly with a container, dismounting the hub-cannula-cap-container assembly from the second subassembly jig, and sealing an opening of the container. The apparatus used for carrying out the method is also disclosed.

2 Claims, 10 Drawing Sheets

METHOD OF MANUFACTURING INJECTION NEEDLES

BACKGROUND OF THE INVENTION

The present invention relates to a method and an apparatus for manufacturing a specific injection needle comprising a hub and a cannula, in which the cannula has a front end projecting from the hub and a back end terminating within the hub.

Conventional injection needles include, as one type, the specific injection needle such as one called "insulin needle" available from Novo Nordisk A/S, which has a specific structure and configuration wherein a cannula having a front end with a sharp bevel and a back end with another sharp bevel inserts in a center hole of a hub in such a manner that the back end projecting inside the hub terminates within the hub (hereinafter, this type of injection needle is merely referred to as injection needle).

The injection needle comprises the cannula and the hub. The cannula of a hub-cannula assembly is covered with a cap, and thereafter the hub-cannula-cap assembly is housed in a hermetically sealed container for subsequent further handling.

One example of the injection needle is illustrated in FIG. 2.

In the injection needle 1 of FIG. 2, a cannula 11 having a front end 13 with a sharp bevel and a back end 14 with another sharp bevel inserts in a center hole of a hub 12 in such a manner that the back end 14 projecting inside the hub 12 terminates within the hub 12.

The hub 12 of the injection needle 1 of FIG. 2 has a bonding area around the center hole for bonding with the cannula 11. The bonding area projects from the rest part of the hub 12 to form a protrusion 12a. The exposed part of the cannula 11 is to be covered by a cap 10 of an elongated cylindrical shape which has an open end 10a and a semi-spherical closed end 10b and is so designed that the open end 10a can be engaged with the protrusion 12a.

The injection needle 1 whose front end 13 has been thus covered with the cap 10 (hub-cannula-cap assembly) is then housed in a container 30 having an opening at one end, and thereafter the opening of the container 30 is sealed with a piece of sealing sheet 31 by means of, for example, heat-sealing.

A process of manufacturing the injection needle 1 should include at least the following work steps or the like:

(a) Adhering the cannula 11 to the hub 12.
(b) Applying silicone oil (hereinafter referred to simply as silicone) to the front end 13 and the back end 14 of the cannula 11 for the purpose of reduction of penetration force.
(c) Covering the front end 13 with the cap 10.
(d) Housing the hub-cannula-cap assembly into the container 30.
(e) Sealing the opening of the container 30 with the sealing sheet 31.

Hitherto, those work steps are performed in a manufacturing line similar to a conventional one for an ordinary injection needle having no sharp bevel projecting inside the hub, with assistance of manual works as occasion demands. However, there are drawbacks of undesirably low work efficiency and impediment to a laborsaving attempt.

The present invention was made in view of the drawbacks of the conventional method and apparatus for manufacturing the injection needle, and an object of the present invention is to provide a novel method and apparatus of manufacturing the injection needle in an efficient and laborsaving manner.

SUMMARY OF THE INVENTION

In accordance with the present invention, there is provided a method of manufacturing an injection needle having a hub with a center hole and a cannula inserting in the center hole, the cannula having a front end with a sharp bevel and a back end with another sharp bevel, the back end terminating within the hub, comprising the steps of:

(a) mounting the hub on a first subassembly jig capable of supporting individually the hub and the cannula in predetermined positions relative to each other, with the front end of the cannula pointed upward;
(b) inserting the cannula into the center hole of the hub to a depth limited by the first subassembly jig;
(c) applying an adhesive to a bonding area of the hub and the cannula;
(d) curing the adhesive in the bonding area to form a hub-cannula assembly;
(e) dismounting the hub-cannula assembly from the first subassembly jig;
(f) applying silicone-containing-liquid to the back end of the cannula of the hub-cannula assembly;
(g) mounting the hub-cannula assembly, whose back end has been coated with silicone-containing-liquid, on a second subassembly jig having a hollow cylindrical rest capable of supporting the hub-cannula assembly by contacting only the hub, with the front end of the cannula pointed upward;
(h) removing excess amount of silicone-containing-liquid remaining within the cannula;
(i) applying silicone-containing-liquid to the front end of the cannula of the hub-cannula assembly;
(j) covering the front end of the cannula with a cap of an elongated cylindrical shape having an open end and a semi-spherical closed end to form a hub-cannula-cap assembly;
(k) housing the hub-cannula-cap assembly into a container having an opening at one end to form a hub-cannula-cap-container assembly;
(l) dismounting the hub-cannula-cap-container assembly from the second subassembly jig; and
(m) sealing the opening of the container of the hub-cannula-cap-container assembly.

In accordance with the present invention, there is also provided an apparatus of manufacturing an injection needle having a hub with a center hole and a cannula inserting in the center hole, the cannula having a front end with a sharp bevel and a back end with another sharp bevel, the back end terminating within the hub, comprising:

(a) a first subassembly jig having a hub-supporting portion and a cannula-supporting portion and being capable of supporting individually plural pairs of the hub and the cannula in one line in such a manner that the hub and the cannula are in predetermined positions relative to each other, with the front end of the cannula pointed upward;
(b) a first conveyor line to transport intermittently the first subassembly jig;

(c) a second subassembly jig having plural hollow cylindrical rests capable of supporting plural pairs of the hub and the cannula in one line by contacting only the hub bonded with the cannula, with the front end of the cannula pointed upward;

(d) a second conveyor line to transport intermittently the second subassembly jig;

(e) a hub-supplying unit provided alongside the first conveyor line;

(f) a cannula-supplying unit provided alongside the first conveyor line;

(g) a hub-cannula-bonding unit, provided alongside the first conveyor line, for adhering the hub and the cannula which has been inserted in the center hole of the hub to a predetermined depth with adhesive;

(h) an adhesive-curing unit, provided alongside the first conveyor line, for heating and drying the hub and the cannula which have been adhered together to form a hub-cannula assembly;

(i) a back-end-coating unit, provided between the first conveyor line and the second conveyor line, for applying silicone-containing-liquid to the back end of the cannula of the hub-cannula assembly;

(j) a handling unit for transferring the hub-cannula assembly by contacting only the hub from the first subassembly jig on the first conveyor line to the back-end-coating unit and further to the second subassembly jig on the second conveyor line;

(k) a back-end-blowing unit, provided alongside the second conveyor line, for supplying air from the front end into the cannula in which silicone-containing-liquid remains so as to blow the remaining liquid out of the back end;

(l) a jig-turn-over unit, provided alongside the second conveyor line, for shifting a direction of the second subassembly jig so as to allow the front end of the cannula to point downward and subsequently upward;

(m) a front-end-coating unit, provided in combination with the jig-turn-over unit, for supplying air from the back end into the cannula and concurrently applying silicone-containing-liquid to the front end of the cannula;

(n) a cap-supplying unit, provided alongside the second conveyor line, for supplying a cap of elongated cylindrical shape having an open end and a semispherical closed end to the front end of the cannula, which has been released from the jig-turn-over unit, mounted on the second subassembly jig in upward pointing attitude in such a manner that the cap is supplied downwardly from above with the open end pointed downward so as to allow the cap to cover the front end of the cannula;

(o) a cap-pressing unit, provided alongside the second conveyor line, for pressing the cap covering the front end of the cannula against the hub to form a hub-cannula-cap assembly;

(p) a container-supplying unit, provided alongside the second conveyor line, for supplying a container having an opening at one end to the hub-cannula-cap assembly, in such a manner that the container is supplied downwardly from above with the opening faced downward so as to allow the container to house the hub-cannula-cap assembly;

(q) a container-pressing unit, provided alongside the second conveyor line, for pressing the container housing the hub-cannula-cap assembly against the second subassembly jig;

(r) a container-sealing unit for sealing the opening of the container housing the hub-cannula-cap assembly with sealing sheet by means of heat-sealing, and for stamping out a heat-sealed piece having a predetermined shape from the sealing sheet; and (s) a container-transferring unit for dismounting the hub-cannula-cap assembly from the second subassembly jig on the second conveyor line and for delivering the hub-cannula-cap assembly to the container-sealing unit.

Thus, in the method and apparatus of the present invention, whole works necessary for manufacturing the injection needle is divided generally into two stages, namely a stage upto the completion of the hub-cannula adhesion and a stage thereafter. On the basis of this conception, the present invention employ the arrangement wherein the first subassembly jig and the second subassembly jig, which are respectively convenient to the operations of the former stage and the latter stage, are moved respectively along the first and second conveyor lines provided separately from each other, and necessary operations are conducted to a row of plural injection needles (including those in a form of parts and in a form of uncompleted assemblies) in one lot.

The first subassembly jig has plural hub-supporting portions and plural cannula-supporting portions and each pair of the hub-supporting portion and the cannula-supporting portion are so designed that the predetermined inserting depth of the cannula is attained when the hub is put on the hub-supporting portion and the back end of the cannula abuts the cannula-supporting portion. Accordingly, for example, no adjustment is required for the inserting depth of the cannula in the adhering step, and the adhering can be carried out easily.

The second subassembly jig has plural hollow cylindrical rests, each of which has internally a relatively large penetrated bore. This arrangement makes it easy to remove the remaining silicone-containing-liquid from the cannula by blowing air through the cannula.

These subassembly jigs in combination with the afore-mentioned arrangement, wherein necessary operations are conducted while plural injection needles in a lot are intermittently moved along the conveyor lines separated into two stages, improve efficiency of not only an individual work step but also overall process.

Further, the operation of each step is simplified, and this makes automatization of the process to be easily designed and enables labor-saving to be accomplished.

DETAILED DESCRIPTION

Embodiments of the invention will now be described by way of example only, in conjunction with the attached drawings.

Figure 1:
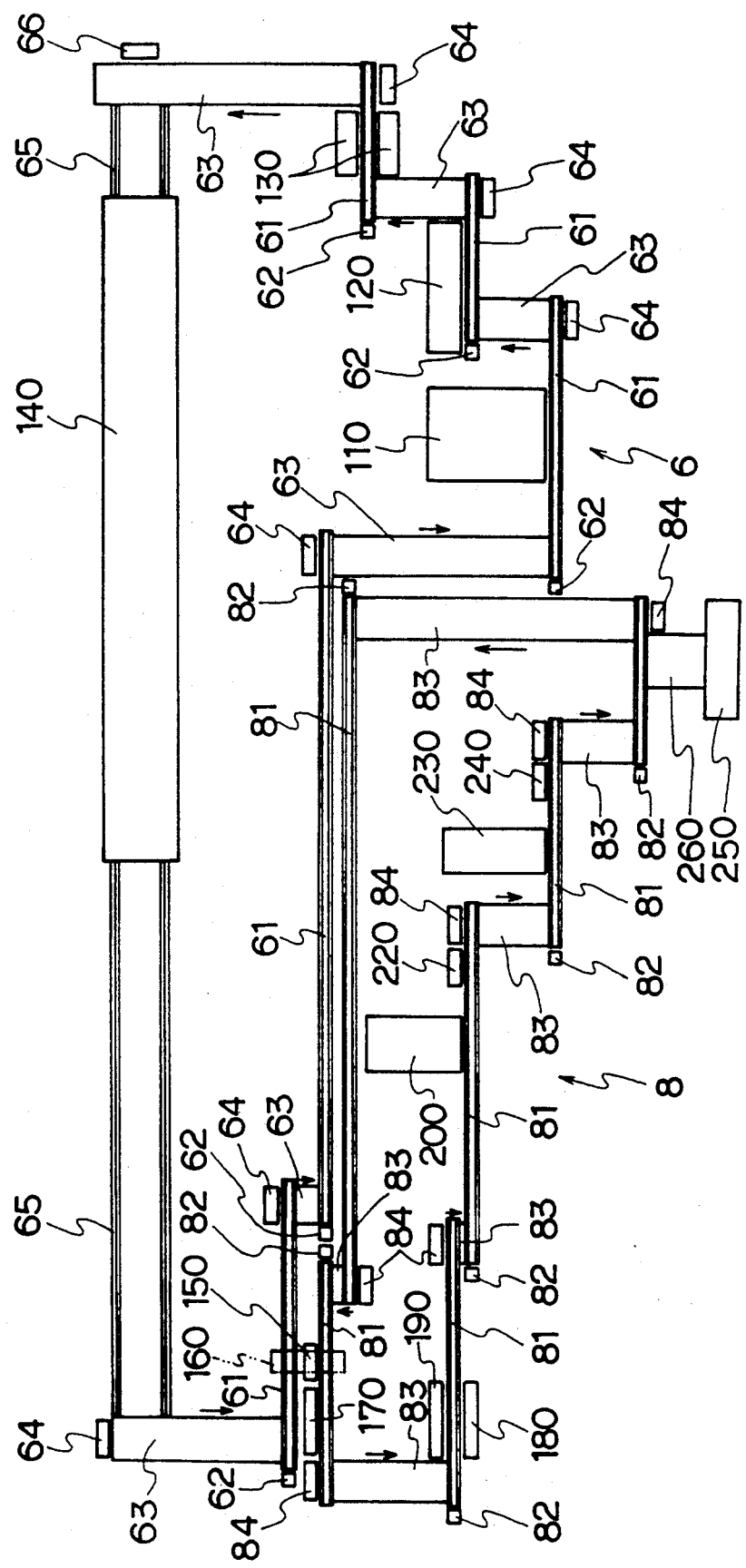
FIG. 1 is a plan view showing a layout of the apparatus of the present invention.
Figure 9:
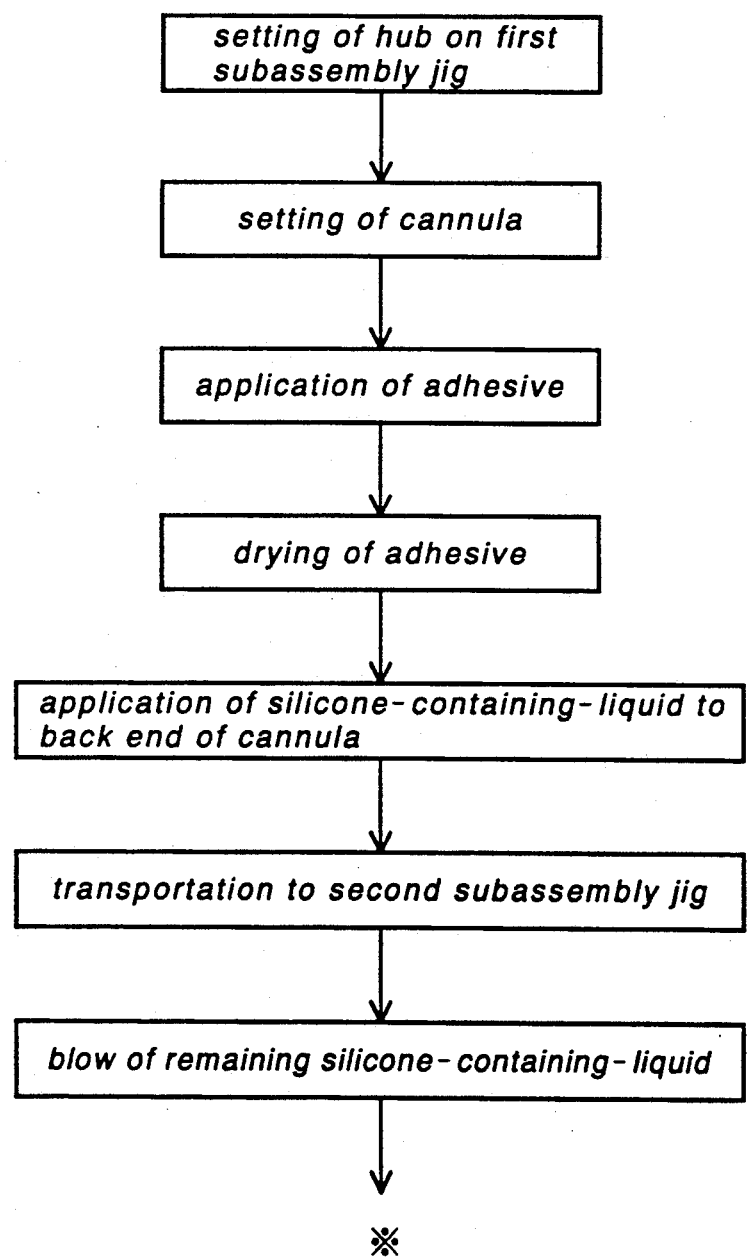
FIGS. 9 to 10 are block diagrams showing example steps of the method of manufacturing an injection needle in accordance with the present invention.
Figure 10:
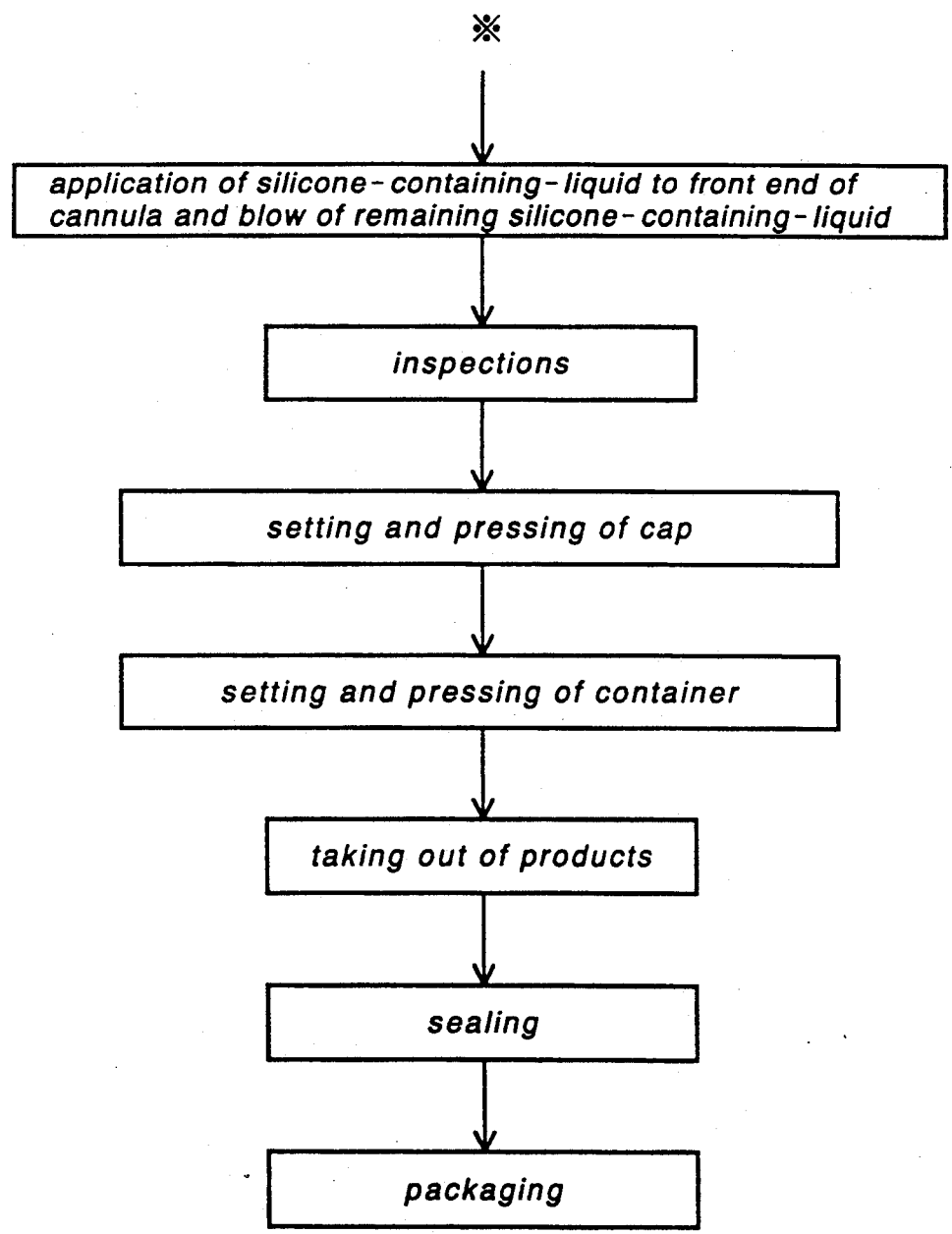

FIG. 1 illustrates an apparatus for performing the steps, for example, shown in FIGS. 9 to 10. In the apparatus, a closed loop of a first conveyor line 6 to convey a first subassembly jig and another closed loop of a second conveyor line 8 to convey a second subassembly jig are arranged side by side.

The first conveyor line 6 comprises:

first longitudinal passages 61 for the first subassembly jig to move toward the row of the injection needles;

first longitudinal drivers 62 for the first subassembly jig to move forward intermittently along the first longitudinal passages 61;

first lateral passages 63 for the first subassembly jig to move in a nearly perpendicular direction against the row of the injection needles;

first lateral drivers 64 for the first subassembly jig to move forward intermittently along the first lateral passages 63;

a conveyor 65 to carry and transport a plurality of the first subassembly jigs; and an auxiliary driver 66 to push the first subassembly jig toward the conveyor 65.

The second conveyor line 8 comprises:

second longitudinal passages 81 for the second subassembly jig to move toward the row of the injection needles;

second longitudinal drivers 82 for the second subassembly jig to move forward intermittently along the second longitudinal passages 81;

second lateral passages 83 for the second subassembly jig to move in a nearly perpendicular direction against the row of the injection needles;

and second lateral drivers 84 for the second subassembly jig to move forward intermittently along the second lateral passages 83.

The operation units of the respective working steps are located alongside the first longitudinal passage 61 or the second longitudinal passage 81. The first longitudinal passage 61 and the second longitudinal passage 81 functions as a guide channel.

The first lateral passage 63 and the second lateral passage 83 are respectively located between the first longitudinal passages 61 and between the second longitudinal passages 81 mentioned above. The first lateral passage 63 and the second lateral passage 83 functions as a buffer capable of absorbing the time-lag of the independent intermittent movements of the subassembly jigs in steps between the first longitudinal passage 61 and the second longitudinal passage 81. Accordingly, as the first lateral passage 63 and the second lateral passage 83, there may be employed for example a belt conveyor having a low-friction surface to allow the subassembly jigs to readily slide.

Alongside the first conveyor line 6, there are provided:

a hub-supplying unit 110;

a cannula-supplying unit 120;

a hub-cannula-bonding unit 130 for adhering a hub and a cannula inserted in the center of the hub to a predetermined depth; and an adhesive-curing unit 140 for heating and drying the hub and the cannula, which have been adhered together, to form a hub-cannula assembly.

Between the first conveyor line 6 and the second conveyor line 8, there are provided:

a back-end-coating unit 150 for applying a liquid in which silicone oil is diluted with a volatile solution (referred to simply as a silicone-containing-liquid in this specification) to the back end of the cannula of the hub-cannula assembly; and a handling unit 160 for transferring the hub-cannula assembly by contacting only the hub from the first subassembly jig on the first conveyor line to the back-end-coating unit and further to the second subassembly jig on the second conveyor line.

Alongside the second conveyor line 8, there are provided:

a back-end-blowing unit 170 for supplying air from the front end into the cannula in which silicone-containing-liquid remains so as to blow the remaining liquid out of the back end;

a jig-turn-over unit 180 for shifting a direction of the second subassembly jig so as to allow the front end of the cannula to point downward and subsequently upward;

a front-end-coating unit 190 provided in combination with the jig-turn-over unit 180 for supplying air from the back end into the cannula and concurrently applying silicone-containing-liquid to the front end of the cannula;

a cap-supplying unit 200 for supplying a cap of elongated cylindrical shape having an open end and a semispherical closed end to the front end of the cannula, which has been released from the jig-turn-over unit 180, mounted on the second subassembly jig in upward pointing attitude in such a manner that the cap is supplied downwardly from above with the open end pointed downward so as to allow the cap to cover the front end of the cannula;

a cap-pressing unit 220 for pressing the cap covering the front end of the cannula against the hub to form a hub-cannula-cap assembly;

a container-supplying unit 230 for supplying a container having an opening at one end to the hub-cannula-cap assembly, in such a manner that the container is supplied downwardly from above with the opening faced downward so as to allow the container to house the hub-cannula-cap assembly; and a container-pressing unit 240, provided alongside the second conveyor line, for pressing the container housing the hub-cannula-cap assembly against the second subassembly jig.

Further, near the second conveyor line 8, there is located a container-sealing unit 250 for covering, the opening of the container housing the hub-cannula-cap assembly with sealing sheet by means of heat-sealing, and for stamping out a heat-sealed piece having a predetermined shape from the sealing sheet. Between the second conveyor line 8 and the container sealing unit 250, there is located a container-transferring unit 260 for dismounting the hub-cannula-cap assembly from the second subassembly jig on the second conveyor line 8 and for delivering the hub-cannula-cap assembly to the container sealing unit 250.

The hub-supplying unit 110 performs a step of mounting the hub on the first subassembly jig capable of supporting individually the hub and the cannula in predetermined positions relative to each other, with the front end of the cannula pointed upward.

The cannula-supplying unit 120 performs a step of inserting the cannula into the center hole of the hub to a depth limited by the first subassembly jig.

The hub-cannula-bonding unit 130 performs a step of applying an adhesive to the bonding area of the hub and the cannula.

The adhesive-curing unit 140 performs a step of curing the adhesive in the bonding area to form a hub-cannula assembly.

The back-end-coating unit 150 performs a step of applying silicone-containing-liquid to the back end of the cannula of the hub-cannula assembly.

The handling unit 160 performs a step of dismounting the hub-cannula assembly from the first subassembly jig and mounting the assembly onto the back-end-coating unit 150, and a step of mounting the hub-cannula assembly, whose back end has been coated with silicone-containing-liquid, on the second subassembly jig having a hollow cylindrical rest capable of supporting the hub-cannula assembly by contacting only the hub, with the front end of the cannula pointed upward.

The back-end-blow unit 170 performs a step of removing excess amount of silicone-containing-liquid remaining within the cannula.

The jig-turn-over unit 180 and the front-end-coating unit 190 perform a step of applying silicone-containing-liquid to the front end of the cannula of the hub-cannula assembly.

The cap-supplying unit 200 and the cap-pressing unit 220 perform a step of covering the front end of the cannula with a cap of an elongated cylindrical shape having an open end and a semi-spherical closed end to form a hub-cannula-cap assembly.

The container-supplying unit 230 and the container-pressing unit 240 perform a step of housing the hub-cannula-cap assembly in a container having an opening at one end to form a hub-cannula-cap-container assembly.

The container-sealing unit 250 performs a step of sealing the opening of the container of the hub-cannula-cap-container assembly.

The container-transferring unit 260 performs a step of dismounting the hub-cannula-cap container assembly from the second subassembly jig and transporting the assembly to the container-sealing unit 250.

Thus, the steps for example shown in FIGS. 9 to 10 are performed.

Figure 3:
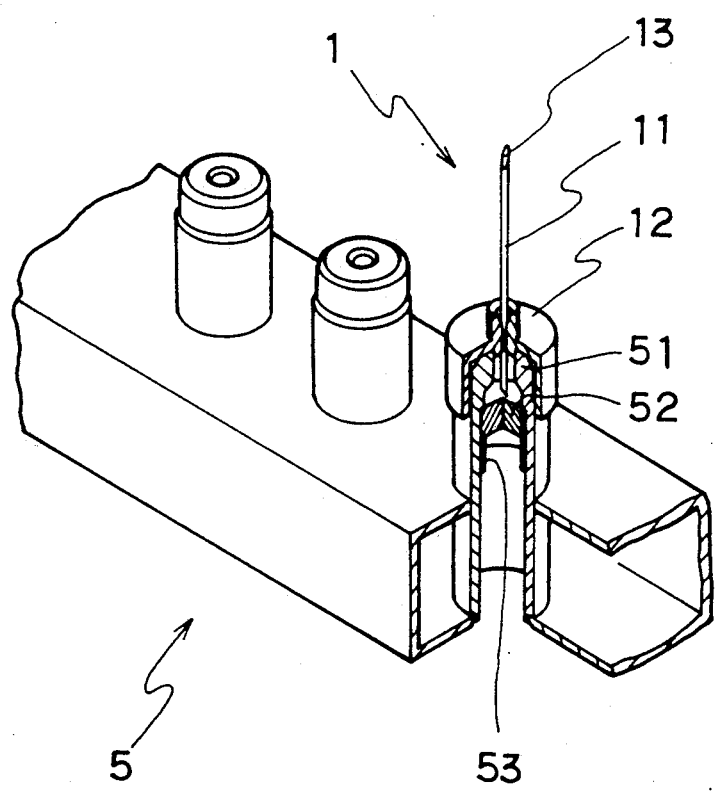
FIG. 3 is a partially-cut-off perspective view showing a first subassembly jig.

The first subassembly jig 5 is, as shown in FIG. 3, so designed that a plurality of injection needles 1 are mounted in a row, with the cannula 11 being inserted into the center hole of the hub 12, and with the front end pointed upward.

The number of the injection needles 1 mounted on one first subassembly jig 5 is typically about 20 to 50. In order to make readily understandable, some omissions and cuttings-away are used appropriately in FIG. 3.

As shown in section in FIG. 3, the first subassembly jig 5 has a hub-supporting portion 51, a cannula-supporting portion 52, and a fixing spring 53 which may be a ring-shaped spring. These components are so designed and arranged that the predetermined inserting depth of the cannula is equal to a depth when the hub 12 is put on the hub-supporting portion 51 and the back end (the lower end) of the cannula 11 abuts the cannula-supporting portion 52.

Figure 4:
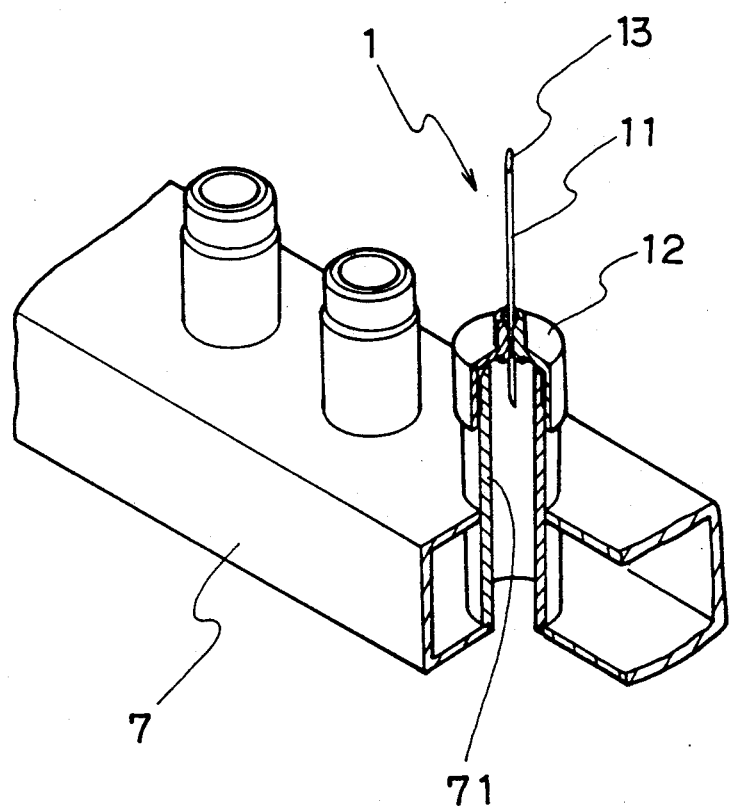
FIG. 4 is a partially-cut-off perspective view showing a socond subassembly jig.

On the other hand, as shown in FIG. 4, the second subassembly jig 7 is to support the hub 12 of the injection needle 1 with the front end of the cannula 11 pointed upward.

One second subassembly jig 7 can carry the same number of the specific injection needles 1 as one first subassembly jig 5.

As shown in section in FIG. 4, the second subassembly jig 7 has a hub-supporting portion (a hollow cylindrical rest) 71 having internally a relatively large penetrated bore.

Figure 5:
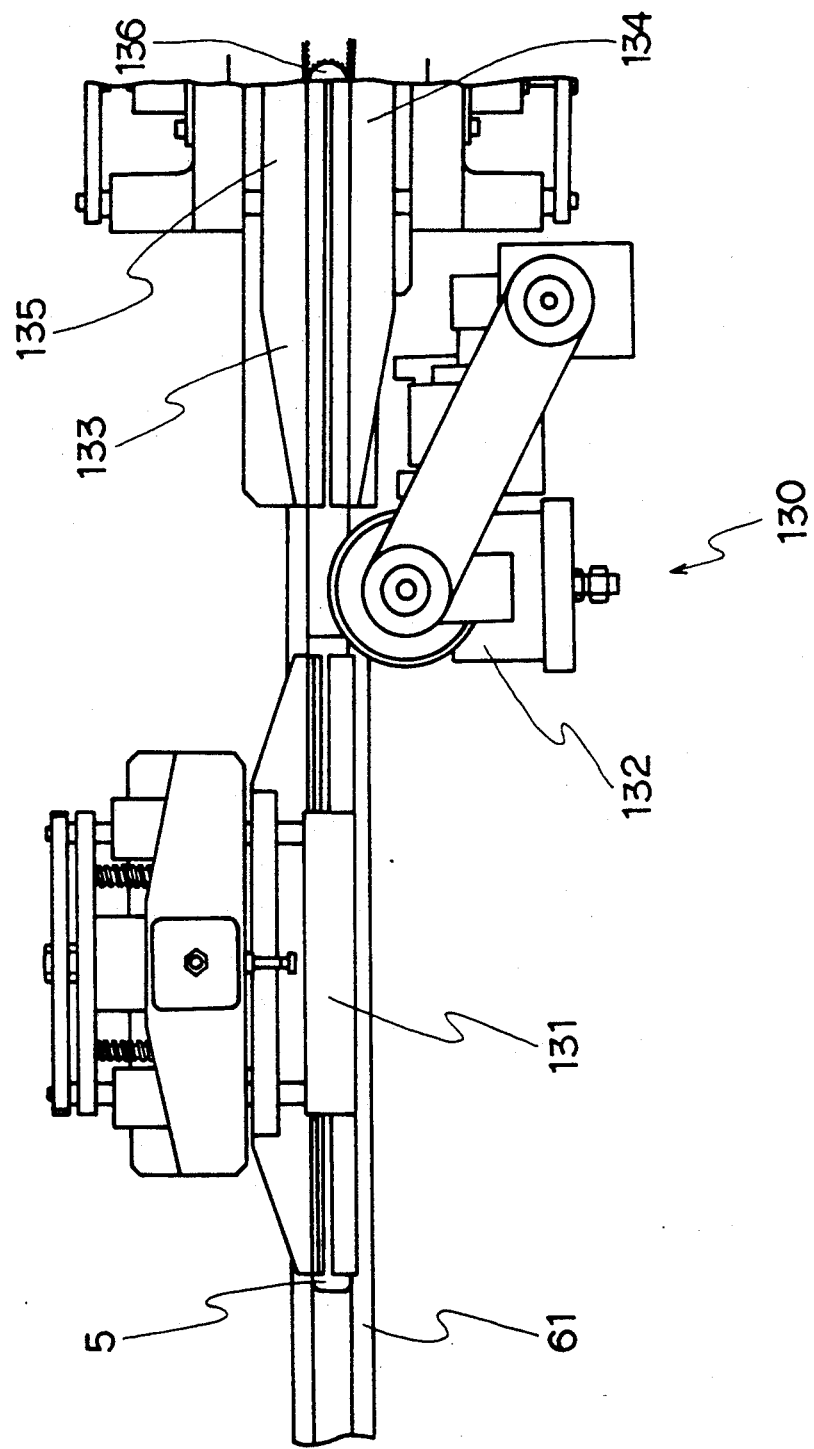
FIG. 5 is a plan view showing an example of the hub-cannula-bonding unit.

FIG. 5 illustrates a hub-cannula-bonding unit 130 comprising a chuck mechanism 131, an adhesive-applying subunit 132, and a cannula-rotating subunit 133.

The chuck mechanism 131 is used in combination with the first longitudinal passage 61 and the first longitudinal driver (not shown). The first longitudinal passage 61 allows the first subassembly jig 5 to move in the longitudinal direction from the left hand side to the right hand side in the drawing, wherein the first subassembly jig 5 carrys plural injection needles in a row whose cannula is inserted through the center hole of the hub with the front end pointed upward. The first longitudinal driver causes the first subassembly jig 5 to move forward intermittently along the first longitudinal passage 61. The chuck mechanism 131 is capable of holding or releasing simultaneously the cannulae of the plural injection needles carried by the first subassembly jig 5 and of moving in the up-down direction against to the first longitudinal passage 61.

The adhesive-applying subunit 132 is provided beside the first longitudinal passage 61 and allowed to move reciprocatively along that passage 61. The subunit 132 applys an adhesive to a portion of each cannula lifted from the hub held by the chuck mechanism 131. The cannula-rotating subunit 133 is located alongside the first longitudinal passage 61 at the downstream of the chuck mechanism 131. The subunit 133 is capable of holding simultaneously the cannulae of the plural injection needles carried by the first subassembly jig 5 and of rotating the cannulae by a predetermined angle against the hubs.

The first subassembly jig 5 carrying the injection needles is introduced one by one to the first longitudinal passage 61 from a buffer area (a first lateral passage) provided close to the first longitudinal passage 61, and delivered intermittently at predetermined intervals by a transport means (a first longitudinal driver) such as an actuator located at the upstream of the first longitudinal passage 61.

In respect of the delivered injection needles, cannulas are pulled out by a fixed length relative to the hubs, and kept at the pulled out positions.

The center hole of the hub has a bore slightly larger than the outer diameter of the cannula with respect to the adhesive application. On the other hand, since the hub engages with a hub-supporting portion 51 of the first subassembly jig 5 (refer to FIG. 3), the hub is supported by the hub-supporting portion 51 and is not pulled out together with the cannula when pulling out the cannula.

Then, the adhesive-applying subunit 132 moves along the first longitudinal passage 61 and applies adhesive on the outer surface of the pulled out cannula.

For example, the adhesive-applying subunit 132 is positioned at the upstream end of the chuck mechanism 131 and faces to the chuck mechanism 131 across the first longitudinal passage 61 when the application of adhesive to all injection needles on one first subassembly jig 5 is completed, that is, when the adhesive-applying step for injection needles on the succeeding first subassembly jig 5 is about to begin.

The adhesive-applying subunit 132 moves to a downstream position as shown in FIG. 5 when the succeeding first subassembly jig 5 is supplied to the front of the chuck mechanism 131.

Then, the adhesive-applying subunit moves to an upstream position while applying adhesive to the plural cannulae in order, after the chuck mechanism 131 pulls out cannulae as stated above.

After application of adhesive is completed, the chuck mechanism 131 capable of going up and down inserts each cannula into a predetermined inserting position and releases the holding of cannulae.

A group of released injection needles put on the first subassembly jig 5 are supplied to the cannula-rotating subunit 133 in order.

The cannula-rotating subunit 133 holds and turns the plural cannulae by means of chucking members 134, 135 which move along the first longitudinal passage 61 at the same speed in opposite directions to each other. The chucking members 134, 135 are interlocked with each other by an interlocking gear. When one of the chucking members is driven by an actuator (not shown), the chucking members 134, 135 move at the same speed in opposite directions to each other as described above.

The hub is engaged with the hub-supporting portion 51 of the first subassembly jig 5 as described above and cannot rotate within the hub-supporting portion 51. Therefore, the cannula rotates relative to the hub when the cannula is held by the chucking members 134, 135 and is rotated.

Adhesive applied to the outer surface of the cannula is uniformly distributed to the outer surface of the cannula by relative rotation between the cannula and the hub.

Figure 6:
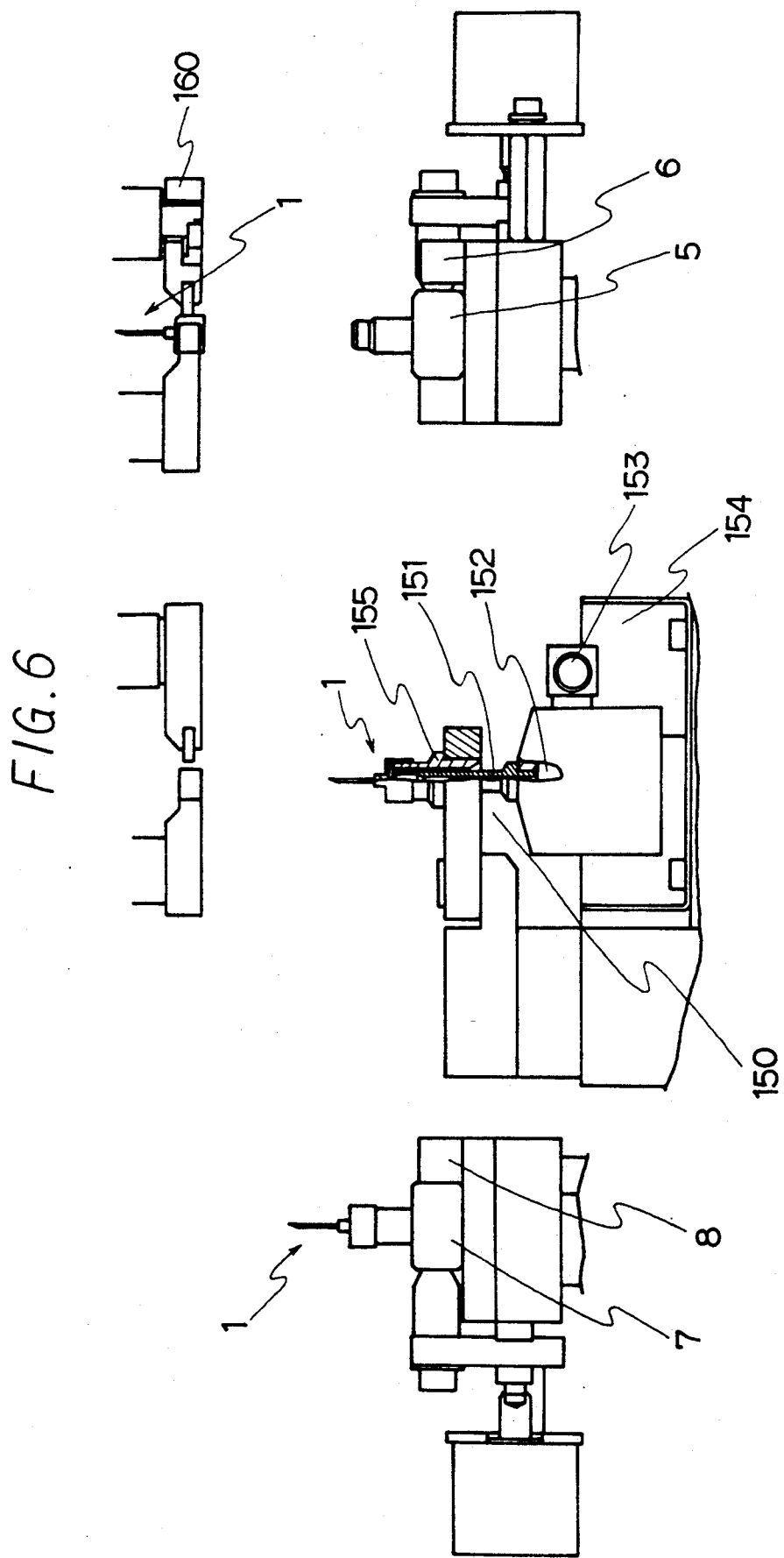
FIG. 6 is a side view showing an example of the back-end-coating unit and an example of the handling unit.

FIG. 6 shows an example of a step of silicone coating to a back end of a cannula during an exchange of a subassembly jig. In FIG. 6, an injection needle 1 is transferred from a first subassembly jig 5 conveyed on a first conveyor line 6 shown in the right portion of FIG. 6 to a back-end-coating unit 150 shown in the central portion of FIG. 6. After silicone coating is carried out, the injection needle 1 is transferred to a second subassembly jig 7 on a second conveyor line 8 shown in the left portion of FIG. 6.

The transference of the injection needle 1 is carried out by a handling unit 160 which handles the injection needle 1 with only contacting a hub of the injection needle 1.

The back-end-coating unit 150 has a chamber of silicone-containing-liquid 152 for connecting a vertically rising pipe 151 and a supplying portion of silicone-containing-liquid (not shown), and a connecting pipe 153. The unit 150 further has a vessel 154 for collecting silicone-containing-liquid overflown from the top of the rising pipe 151, and an outer tube 155 supporting a hub and surely preventing adhesion or stain of silicone-containing-liquid to the hub.

In the back-end-coating unit 150, silicone-containing-liquid is overflown at a constant rate of flow from an uppermost end or top open end of the rising pipe 151 having an inner diameter larger than an outer diameter of the cannula 11 and having an outer diameter smaller than an inner diameter of the hub 12. Silicone is coated on the back end 14 of the injection needle 1 by dipping the back end 14 into silicone-containing-liquid at the uppermost end of the rising pipe 151.

The above-mentioned dipping is carried out by the handling unit 160 which handles the injection needle 1 with only contacting a hub 12 of the injection needle 1.

In the preferred embodiment, about 20 to 50 injection needles 1 are arranged in a row and handled, so that silicone coating to back ends 14 is carreid out at one time. In this case, there are provided rising pipes 15 whose number corresponds to that of arranged injection needles 1.

Silicone-containing-liquid is supplied from a supplying portion of silicone-containing-liquid (not shown) to a lower portion of the rising pipe 151 at a constant rate of flow. As a supplying portion of silicone-containing-liquid, fixed delivery pumps such as plunger pumps and diaphragm pumps can be used. However, usable pumps are not limited thereto in the present invention.

The supply of silicone-containing-liquid of 10 to 30 ml/min is enough for one rising pipe in the case of, for example, a rising pipe 151 of which uppermost opening has an inner diameter of 4 mm and an outer diameter of 5 mm (the intermediate portion of the rising pipe is thinned to 3 mm). In general the supply amount of about 20 ml/min is employed. Flow velocity of this supply amount is 1.33 to 3.98 cm/sec on the basis of an inner diameter of the above rising pipe.

When the supply of silicone-containing-liquid is too small, renewal of silicone-containing-liquid becomes insufficient. On the other hand, when it is too large, there is a danger that silicone-containing-liquid adheres to the inner surface of the hub on overflowing silicone-containing-liquid.

When a large number of injection needles 1 are coated with silicone at one time as stated above, silicone-containing-liquid can be supplied, for example, to all rising pipes 151 from one supplying unit of silicone-containing-liquid.

Viscosity of the above-mentioned silicone-containing-liquid is preferably from about 20 to 100 cP. When viscosity is too low, coating of silicone becomes insufficient. On the other hand, when viscosity is too high, coating of silicone becomes difficult and finally silicone in particle condition adheres to the cannula.

In the back-end-coating unit 150, it is possible to recover overflown silicone-containing-liquid while coating the back end 14 with silicone oil and to recycle the recovered silicone-containing-liquid after adjustment of composition, adjustment of viscosity removal of impurities and the like are carried out at need.

Silicone-containing-liquid is overflown with forming a certain adequate shape enabling the dipping of the back end 14 without contacting the inner surface of the hub. Accordingly, silicone is sufficiently coated on the back end 14 with silicone-containing-liquid of which composition, viscosity and the like are always kept in an adequate condition and which does not contain impurities, so that shortage of silicone or adhesion of foreign matter is not caused. Further, adhesion of silicone-containing-liquid to the inner surface of the hub is certainly avoided.

Figure 7:
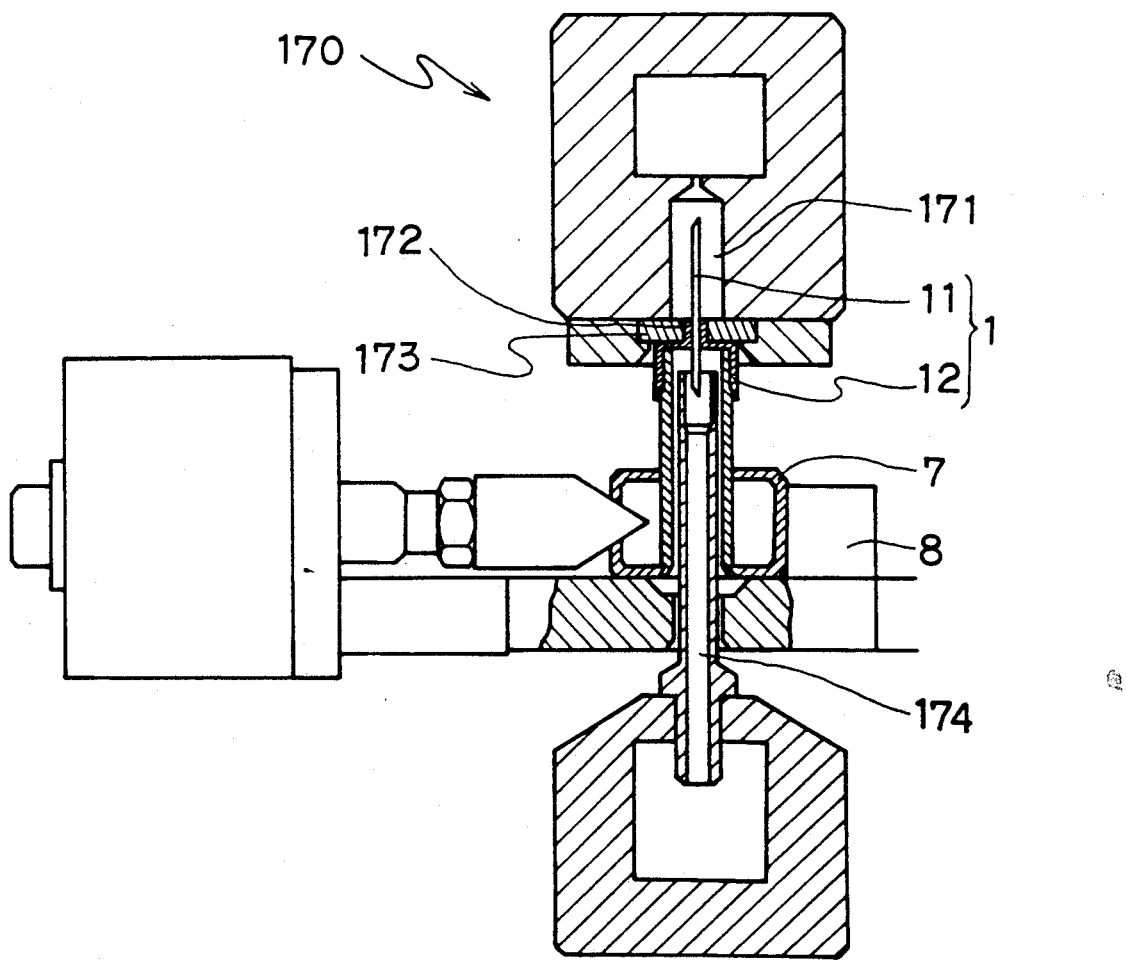
FIG. 7 is a side view partially in section showing an example of the back-end-blowing unit.

The injection needle 1, which is tranferred from the back-end-coating unit 150 to the second subassembly jig 7 by the handling unit 160, is conveyed along a second conveyor line 8 to a back-end-blowing unit 170 shown in FIG. 7.

When the injection needle 1 is transferred to the second subassembly jig 7 by the handling unit 160, removal of silicone-containing-liquid remaining within the back end might be carried out by the back-end-blowing unit 170.

As shown in FIG. 7, the back-end-blowing unit 170 comprises a gas chamber 171 having an opening 172 capable of closely contacting the front side surface of the hub 12, a gas-supplying portion (not shown) for supplying compressed gas to the gas chamber 171, and a drain pipe 174 put on the back end of the cannula 11 without contacting it. The opening 172 has an inner diameter which is larger than the outer diameter of the cannula 11 and smaller than the outer diameter of the hub 12. The drain pipe 174 has an inner diameter larger than the outer diameter of the cannula 11 and an outer diameter smaller than the inner diameter of the hub 12.

Around the opening 172 there is provided an abutting member 173 comprising rubber-like elastic material, which is rich in flexibility to keep airtightness, such as silicone rubber, urethane rubber and nitrile rubber.

Gas is introduced into the cannula 11 from the front end thereof using the above-mentioned back-end-blowing unit 170, and silicone-containing-liquid remaining within the cannula 11 is blown out and discharged from the back end. As a gas used for blowing, dry and clear air can be used. A pressure of supplied gas is about 1 to 3 kg/cm² G.

Figure 8:
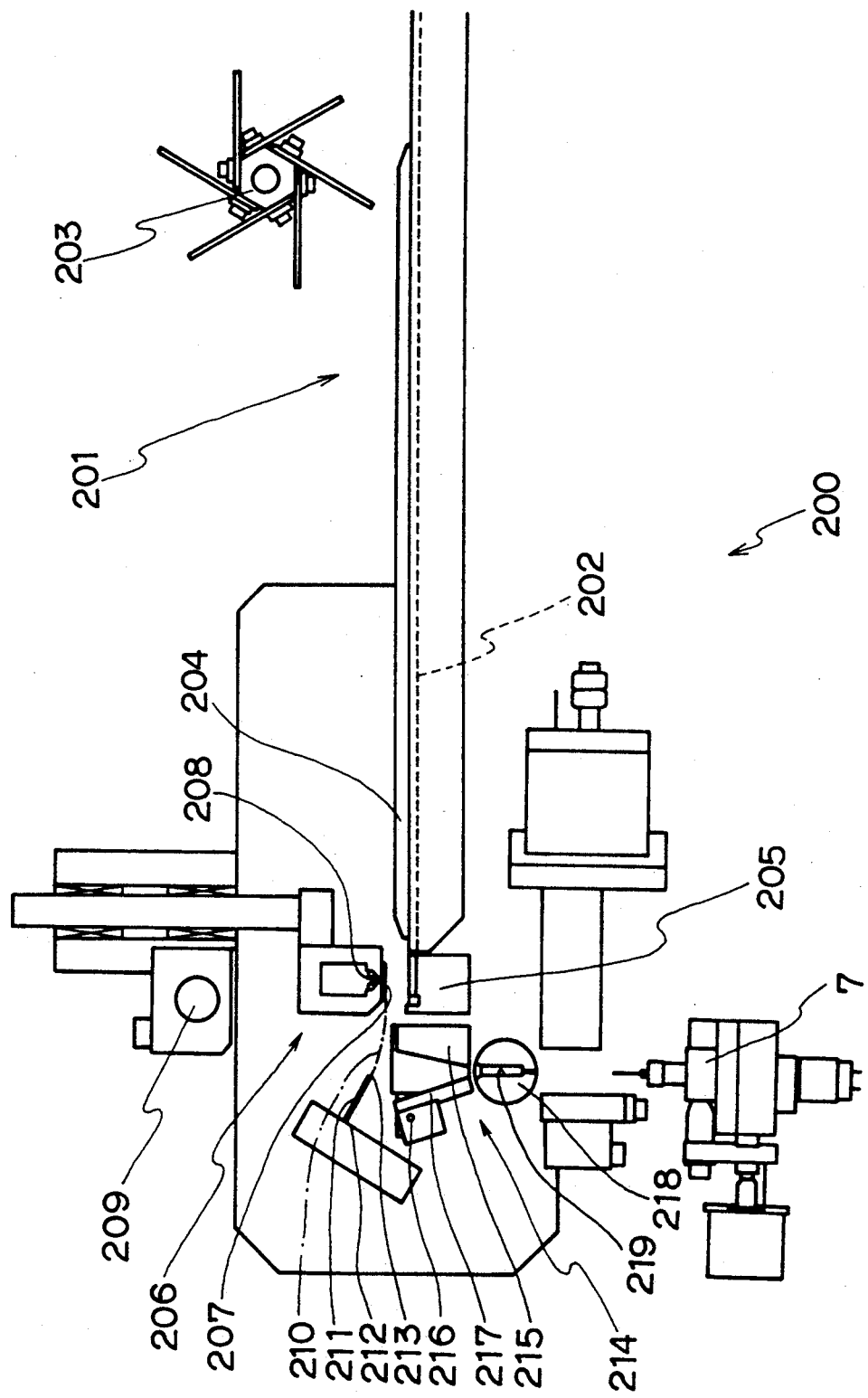
FIG. 8 is a side view showing an example of the cap-supplying unit.

FIG. 8 is a side view of an example of a cap supplying unit 200.

In FIG. 8, an injection needle is put on the second subassembly jig 7 with pointing exposed cannula upward.

The cap-supplying unit 200 shown in FIG. 8 comprises
(a) an arranging subunit 201 having a guide groove 202 for supporting a cap with coinciding a longitudinal direction of the cap with a predetermined direction, and a feeder 203 for moving a supported cap along the guide groove 202,
(b) a cap receiver 205 connected to a downstream end of the guide groove 202,
(c) a cap-transferring subunit 206 for holding by suction a cap on the cap receiver 205 from above, and for transferring the cap in a direction of axis along a circular orbit 210 which gradually rises from a horizontal condition,
(d) a hopper 214 positioned adjacent to the cap receiver 205 in the longitudinal direction of the guide groove 202 and having inclined surfaces 215, 217,
(e) a limit bar 211 having a fixed end 212 and a free end 213 and having a section smaller than a section of an opening of the cap, and being positioned above the hopper 214, a distance between the free end 213 and end of the hopper 214 on the side of the cap receiver 205 being designed to be shorter than a length of the cap, the free end 213 being positioned above the circular orbit 210, the fixed end 212 being so positioned as to coincide with a tangential direction of the circular orbit 210 of the free end 213 and as to be above the free end 213, and
(f) a cap-turn-over subunit 218 positioned below the hopper 214 and having a cap-receiving recess 219, an attitude of the cap-turn-over subunit being changeable between an attitude wherein an opening of the cap-receiving recess 219 points upward and an attitude wherein an opening of the cap-receiving recess 219 points downward.

The tilt angle of the limit bar 5 to a horizontal direction is preferably form 20° to 40°, more preferably from 25° to 35°.

In the above-mentioned apparatus, a cap of which longitudinal direction is lined up is held by suction by the cap-transferring subunit 206 from above, and the limit bar 211 is moved along the circular orbit 210 in the longitudinal direction of the cap.

The cap is transferred with its opening end at the head, and the free end 213 of the limit bar 211 goes into the opening. Then, the cap advances obliquely and upward along the tangential direction by the guide of the limit bar 211. When the cap-transferring subunit 206 moves to a predetermined position, the cap is released from holding by the cap-transferring subunit 206 so that the cap departs from the subunit 206. Next, the cap begins to descent obliquely and downward toward the free end 213 of the limit bar 211, and falls into the hopper 214 with a semi-spherical closed end of the cap pointed downward.

On the other hand, with respect to a cap transferred with its semi-spherical closed end at the head, the advancement of the cap is stopped since the free end 213 of the limit bar 211 contacts with the semi-spherical closed end. Further, when the cap-transferring subunit 206 moves to a predetermined position, the cap is released from the holding by the cap-transferring subunit 206 so that the cap departs from the subunit 206. At this time the back end of the cap does not come to a position above the hopper 214 so that the cap falls into the hopper 214 with a semi-spherical closed end of the cap pointed downward.

The cap, which passes through the hopper 214 with its semi-spherical closed end at the head, is received in the cap-receiving recess 219 of the cap-turn-over subunit 218. Thereafter, the cap is supplied on the cannula via, for example, a cap guide (not shown) and the like with its opening end pointed downward by the turn-over of the cap turn-over subunit 218.

In the above-mentioned apparatus there are carried out the steps of
(a) lining up a longitudinal direction of a cap,
(b) holding the cap by suction from above, transferring the cap in the longitudinal direction of the cap along a specific circular orbit 210 rising gradually from a horizontal direction (the limit bar 211 is positioned oblieqly and upward in the approximately tangential direction to the orbit), releasing the holding of the cap when the cap-transferring subunit 206 moves to a predetermined position and falls the cap with its semi-spherical closed end pointed downward, and
(c) changing an attitude of the cap which falls approximately vertically with its opening end pointed downward.

Figure 2:
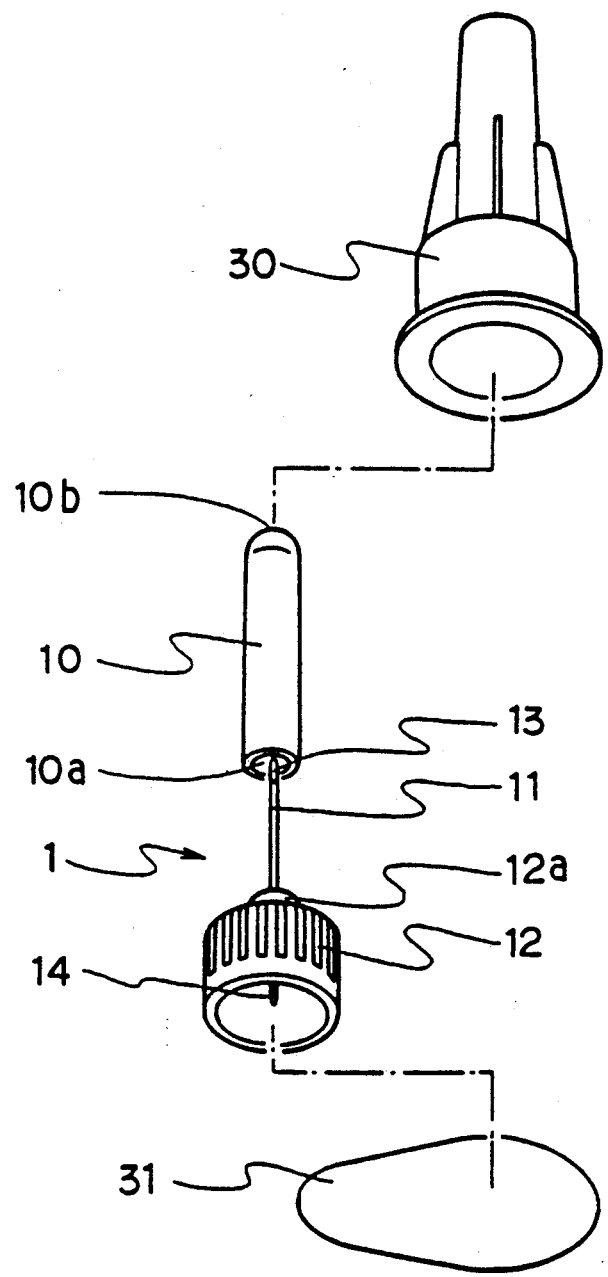
FIG. 2 is a perspective view of an example of the injection needle assembly.

In the apparatus of FIGS. 1 to 2, about 20 to 50 caps are supplied to the same number of exposed cannulae of injection needles.

The feeder 203 of the arranging subunit 201 is so designed as to be adjustable up and down, and is rotated counterclockwise in FIG. 8. A cover 204 for covering the guide groove 202 is provided at the downstream side (left side) of the feeder 203. Caps, which are supplied at random to the upstream side (right side) of the feeder 203, are compulsorily moved in the guide groove 202 toward the cap-receiving portion 205. The longitudinal directions of caps are coincided with movement direction during movement of the caps. Further, when the longitudical directions of caps do not coincide with movement direction of caps, caps are moved in the guide groove 202 repeatedly till they coincide with movement direction of caps.

The cap-transferring subunit 206 for holding caps by suction from above, which have reached the cap-receiving portion 205, has a holding portion 207 for holding caps by suction in grooves by the use of negative pressure, and a vacuum port 208 for maintaining the inside of the holding portion 207 at negative pressure. The cap-transferring subunit 206 rotates about the shaft 209. Accordingly, caps held by the holding portion 207 are transferred along the circular orbit 210 in the longitudinal direction of caps.

The vacuum port 208 is so designed that positive pressure is given to the vacuum port 208 by a signal from outside and releases the cap from the holding portion 207. By employing such constitution, it is avoided that a cap is supplied on an empty subassembly jig from which an injection needle is removed by inspection from a manufacturing line in a former step, specificly when caps are supplied to plural injection needles simultaneously.

It is possible to employ a constitution wherein a cap-receiving portion 205 is omitted, the guide groove 202 of the arranging subunit 201 is extended to the hopper 214, and another cap-transferring subunit is provided in the midway of the extended guide groove, whereby caps are intermittently fed by a predetermined distance in their longitudinal directions.

In the apparatus shown in FIG. 8, the limit bar 211 is so positioned that center of gravity of a cap whose head is at a free end of the limit bar 211 is situated above the hopper 214. In the apparatus, on the other hand, wherein caps moves in the guide groove 202, the limit bar 211 is so positioned that center of gravity of a cap whose head is at a free end of the limit bar 211 is situated on the guide groove 202 (near the end of the guide groove).

The hopper 214, into which caps fall with their semi-spherical closed ends pointed downward by the function of the limit bar 211, has a first slope 215 and a second slope 217. The passage of caps has a rectangular section.

Though the first slope 215 may be a vertical surface, the first slope 215 preferably has sufficient area to allow a cap to rotate about an end of the cap and is formed in such shape that enables introduction of caps to the turn-over subunit 218.

Further, in the example shown in FIG. 8, the second slope 217 is made rotatable about the shaft 216 at least clockwise, that is, the second slope 217 is capable of opening and closing. The second slope 217 is so designed as to open and close before receiving the next cap, and so it is possible to discharge a cap which cannot pass through smoothly and remains within the hopper, and to supply the next cap smoothly.

The cap-turn-over subunit 218 has also a function to control timing for supplying caps to injection needles.

In the cap-supplying unit 200, it is possible, instead of the limit bar 211 and hopper 214, to employ a selective turn-over subunit which has a receiving recess with a central bar, and receives only caps supplied with their opening ends at the head and then turns over the caps. In this case, caps from the arranging subunit 201 are introduced to the selective turn-over subunit, and then supplied to the cap turn-over subunit 218 after all caps are lined up with their semi-spherical closed ends at the head.

Caps are put on front ends of injection needles pointing upward in the manner as stated above. Attachement of caps to the injection needles (hub-cannula assemblies) is finished by pushing semi-spherical closed ends of caps positioned at the top towards hubs by means of, for example, another pushing means.

With respect to a hub-supplying unit 110, a cannula-supplying unit 120, an adhesive-curing unit 140, a jig-turn-over unit 180, a front-end-coating unit 190, a cap-pressing unit 220, a container-supplying unit 230, a container-pressing unit 240, a container-sealing unit 250 and a container-transferring unit 260, it is possible to employ such apparatus that have been used for manufacturing general injection needles.

As described above, according to the present invention, there are provided a method and an apparatus enabling efficient production and reduction of labor when manufacturing injection needles having back ends which terminate within hubs.

What is claimed is:

1. A method of manufacturing an injection needle having a hub with a center hole and a cannula inserting in the center hole, the cannula having a front end with a sharp bevel and a back end with another sharp bevel, the back end terminating within the hub, comprising the steps of:
   (a) mounting the hub on a first subassembly jig capable of supporting individually the hub and the cannula in predetermined positions relative to each other, with the front end of the cannula pointed upward;
   (b) inserting the cannula into the center hole of the hub to a depth limited by the first subassembly jig;
   (c) applying an adhesive to a bonding area of the hub and the cannula;
   (d) curing the adhesive in the bonding area to form a hub-cannula assembly;
   (e) dismounting the hub-cannula assembly from the first subassembly jig;
   (f) applying silicone-containing-liquid to the back end of the cannula of the hub-cannula assembly;
   (g) mounting the hub-cannula assembly, whose back end has been coated with silicone-containing-liquid, on a second subassembly jig having a hollow cylindrical rest capable of supporting the hub-cannula assembly by contacting only the hub, with the front end of the cannula pointed upward;
   (h) removing excess amount of silicone-containing-liquid within the cannula;
   (i) applying silicone-containing-liquid to the front end of the cannula of the hub-cannula assembly;
   (j) covering the front end of the cannula with a cap of an elongated cylindrical shape having an open end and a semi-spherical closed end to form a hub-cannula-cap assembly;
   (k) housing the hub-cannula-cap assembly into a container having an opening at one end to form a hub-cannula-cap-container assembly;
   (l) dismounting the hub-cannula-cap-container assembly from the second subassembly jig; and
   (m) sealing the opening of the container of the hub-cannula-cap-container assembly.

2. A method of claim 1, wherein the step of applying silicone-containing-liquid to the back end is a step of allowing silicone-containing-liquid to continue overflowing from a top end of a vertically rising pipe having an inside diameter larger than an outside diameter of the cannula and an outside diameter smaller than an inside diameter of the hub, and of concurrently dipping the back end into silicone-containing-liquid at the top end of the rising pipe.

* * * * *